United States Patent [19]
Oshio et al.

[11] Patent Number: 4,996,379
[45] Date of Patent: Feb. 26, 1991

[54] METHOD OF PREPARING 1,1,1,2-TETRAFLUOROETHANE FROM 1,1-DICHLORO-1,2,2,2-TETRAFLUOROETHANE

[75] Inventors: Hideki Oshio, Omiya; Sadaharu Mishumi, Kawagoe; Kiyoshi Yagii, Fujimi; Satoshi Yoshikawa, Saitama; Katsuyoshi Murata, Kawagoe, all of Japan

[73] Assignee: Central Glass Company, Limited, Ube, Japan

[21] Appl. No.: 357,291

[22] Filed: May 26, 1989

[30] Foreign Application Priority Data

May 30, 1988 [JP] Japan .................................. 63-132395
Dec. 19, 1988 [JP] Japan .................................. 63-320077
Dec. 23, 1988 [JP] Japan .................................. 63-324998
Jan. 13, 1989 [JP] Japan ....................................... 1-7056

[51] Int. Cl.$^5$ ...................... C07C 17/10; C07C 19/08; C07C 17/08
[52] U.S. Cl. .................................. 570/176; 570/151; 570/166; 570/169
[58] Field of Search ................. 570/176, 166, 169, 151

[56] References Cited

U.S. PATENT DOCUMENTS 2,748,177  5/1956  Miller et al. .......................... 570/166
3,087,974  4/1963  Hauptschein et al. ............... 570/151
3,650,987  3/1972  Vecchio et al. ...................... 570/166

FOREIGN PATENT DOCUMENTS 1578933  11/1980  United Kingdom ................ 570/176

OTHER PUBLICATIONS

"Studies on a Vapour-Phase for the Manufacture of Chlorofluoroethanes", by M. Vecchio et al., Journal of Fluorine Chemistry, 4 (1974), pp. 117–139.
"Catalyst for Fluorination of Organic Chlorocompounds", by L. Marangoni et al., Chim. Ind. (Milan), 64, pp. 135–139 (1982).

*Primary Examiner*—Alan Siegel
*Attorney, Agent, or Firm*—Fleit, Jacobson, Cohn, Price, Holman & Stern

[57] ABSTRACT

1,1,1,2-Tetrafluoroethane, a refrigerant, is formed with little formation of isomers or chlorofluoroethanes having not very different boiling points by reacting 1,1-dichloro-1,2,2,2-tetrafluoroethane (R-114a), which may contain up to about 25 wt% of 1,2-dichloro-1,1,2,2-tetrafluoroethane (R-114), with hydrogen gas in the presence of a palladium-on-active alumina catalyst at a temperature lower than 200° C. and not lower than 120° C. R-114a almost free of R-114 is obtained by reacting 1,1,1-trichloro-2,2,2-trifluoroethane with hydrogen fluoride in vapor phase in the presence of a catalyst prepared by partially fluorinating γ-alumina by treatment with hydrogen fluoride gas.

14 Claims, No Drawings

METHOD OF PREPARING 1,1,1,2-TETRAFLUOROETHANE FROM 1,1-DICHLORO-1,2,2,2-TETRAFLUOROETHANE

BACKGROUND OF THE INVENTION

This invention relates to a method of preparing 1,1,1,2-tetrafluoroethane, which is useful as a refrigerant having adequate stability, by hydrogenating 1,1-dichloro-1,2,2,2-tetrafluoroethane using a palladium catalyst.

It is known that 1,1,1,2-tetrafluoroethane (hereinafter referred to as R-134a) can be obtained by fluorinating 1-chloro-2,2,2-trifluoroethane by hydrogen fluoride in the presence of a chromium oxide catalyst, but the yield of R-134a is only about 10–30%. There is a proposal of accomplishing the fluorination in a liquid phase by using potassium fluoride, but this reaction must be made under high temperature and high pressure conditions and forms potassium chloride as an inconvenient by-product. Also it is known that R-134a is obtained at fairly high yield by fluorinating trifluoroethylene by hydrogen fluoride in the presence of a chromium oxyfluoride catalyst, but trifluoroethylene is a costly material.

JP 56-38131 shows obtaining R-134a from 1,1-dichloro-1,2,2,2-tetrafluoroethane (referred to as R-114a) by reaction with hydrogen in the presence of a palladium-on-active carbon catalyst. The hydrogenation process is applicable also to 1-chloro-1,2,2,2-tetrafluoroethane (referred to as R-124), but R-124 is a costly material. In the case of the hydrogenation of R-114a the yield of R-134a reaches about 70%, but the selectivity of the reaction to R-134a is lower than 80%. That is, the reaction product includes about 10% of R-124 and about 10% of 1,1,1-trifluoroethane (referred to as R-143a). Besides, when the starting R-114a contains its isomer, 1,2-dichloro-1,1,2,2-tetrafluoroethane (referred to as R-114), by-products of the hydrogenation process include 1,1,2,2-tetrafluoroethane (referred to as R-134) and 1-chloro-1,1,2,2-tetrafluoroethane (referred as R-124a).

R-134a has a boiling point of $-26.5°$ C. When the reaction product of the hydrogenation process includes by-products having boiling points close to this boiling point, such as R-134 (b.p. $-19.7°$ C.), R-124 (b.p. $-12°$ C.) and/or R-124a (b.p. $-10.2°$ C.), difficulties are offered to the separation and purification of R-134a. For example, about 40-stage distillation towers are necessary for completely separating R-134a from R-124 by an ordinary distillation method, and by this method neither separation of R-134a from R-134 nor separation of R-124 from R-124a can be accomplished. Therefore, in the industrial practice of the hydrogenation of R-114a to R-134a there are serious problems about enhancing purity of obtained R-134a and returning by-produced R-124, which is regarded as a precursor of R-134a, to the reaction system.

As an industrial material, R-114a is usually prepared by fluorinating 1,1,2-trichloro-1,2,2-trifluoroethane (referred to as R-113) or 1,1,1-trichloro-2,2,2-trifluoroethane (referred as R-113a) with hydrogen fluoride. By this method it is inevitable that the obtained R-114a contains about 10–25% of R-114. It is very difficult to separate R-114 from R-114a by distillation since the difference between the boiling points of the respective compounds is only $0.6°$ C.

For the vapor phase fluorination of R-113 or R-113a it is necessary to use a catalyst such as aluminum fluoride (J. Fluorine Chem, 4, 117(1974)) or chromium oxide (Chim. Ind. (Milan), 64, 135(1982)). However, aluminum fluoride is not high in the catalytic activity, and chromium oxide has toxicity and hence raises the problem about the pollution of the environment.

SUMMARY OF THE INVENTION

It is an object of the invention to provide an improved method of preparing R-134a by hydrogenation of R-114a, which method is high in the selectivity of the hydrogenating reaction to R-134a and is practicable even though a considerable amount of R-114 coexists with the starting R-114a.

According to the invention there is provided a method of preparing 1,1,1,2-tetrafluoroethane (R-134a), comprising reacting 1,1-dichloro-1,2,2,2-tetrafluoroethane (R-114a) with hydrogen gas in the presence of a palladium-on-active alumina catalyst at a temperature lower than 200° C. and not lower than 120° C.

By using palladium carried on active alumina as the hydrogenation catalyst and performing the hydrogenation reaction at temperatures within the above limitations, both the conversion of the starting R-114a and the selectivity to R-134a are remarkably enhanced. The catalyst employed in this invention exhibits very high selectivity to R-134a compared with the palladium-on-active carbon catalyst used in the known method. It is a matter of course that even in this method it is desirable that the coexistence of R-114 with R-114a be as little as possible. However, even when R-114a containing up to about 25% of R-114 is used this method is fully practicable and gives R-134a at a fairly good yield with a success in decreasing obstructive by-products such as R-134, R-124 and R-124a.

The present invention includes a method of preparing R-114a for use as the starting material of R-134a. The method comprises reacting 1,1,1-trichloro-2,2,2-trifluoroethane (R-113a) with hydrogen fluoride in vapor phase in the presence of a catalyst comprising γ-alumina partially fluorinated by treatment with hydrogen fluoride. By this method R-113a is efficiently converted in R-114a with very high selectivity, and the formation of undesirable by-products such as R-114 and chloropentafluoroethane (referred to as R-115) is remarkably reduced.

As an industrial material, 1,1,2-trichloro-1,2,2-trifluoroethane (R-113) is more readily available than R-113a. It is possible to fluorinate R-113 to R-114a as mentioned hereinbefore, but it is inevitable that a considerable amount of R-114 is by-produced.

The present invention includes a method of preparing R-114a from R-113 with little formation of R-114. The method comprises the steps of isomerizing R-113 to R-113a and then reacting R-113a obtained at the isomerization step with hydrogen fluoride in the presence of a catalyst such as γ-alumina partially fluorinated by treatment with hydrogen fluoride.

DESCRIPTION OF THE PREFERRED EMBODIMENTS

In preparing R-134a by the hydrogenation method according to the invention it is suitable to use 2 to 4 mols of hydrogen per mol of R-114a (or a mixture of R-114a and R-114). If the amount of hydrogen is less than 2 mols the conversion of R-114a remains low, whereby the yield of R-134a is low. However, it is uneconomical to use more than 4 mols of hydrogen because the conversion of R-114a no longer augments so that a large amount of hydrogen has to be recovered. The reaction is carried out at a temperature not lower than 120° C. because at lower temperatures the conversion of R-114a remains low whereby the yield of R-134a is low. However, the reaction temperature should be lower than 200° C. because otherwise the selectivity of the reaction to R-134a lowers by a considerable increase in the formation of R-124 and also R-134.

It is essential to use a palladium-on-active alumina catalyst. The content of palladium in the catalyst is not strictly limited, though it is preferable that the content of palladium falls in the range from 0.2 to 5 wt %.

Preferably the catalyst is pretreated with R-114a or a mixture of R-114a and R-114 to thereby partially fluorinate the active alumina used as the carrier of the catalyst, because by this treatment the formation of excessively hydrogenated 1,1,1-trifluoroethane (R-143a) can be reduced. It is suitable to perform the pretreatment at a temperature of about 200° C. or above for about 20 hr. For example, when the product of the hydrogenation reaction using the catalyst without pretreatment contains about 10% of R-143a the pretreatment of the catalyst has the effect of decreasing the amount of R-143a to about 5%, though the effect of the pretreatment is variable according to the conditions of the hydrogenation reaction.

It is suitable to perform the catalytic contact reaction between R-114a and hydrogen such that the contact time falls in the range from 5 to 30 sec. If the contact time is shorter than 5 sec the conversion of R-114a remains low whereby the yield of R-134a is low. If the contact time is longer than 30 sec the yield of R-134a per unit quantity of the catalyst lowers.

R-134a formed by the above described reaction can be separated from unreacted starting material and by-products and purified by a known method such as distillation. Among the by-products, R-124 may be returned to the reaction system since it is a precursor of R-134a.

EXAMPLES 1–4

For contact reaction of a mixture of R-114a and R-114 with hydrogen gas, a reaction tube of heat resistant glass having an inner diameter of 2.5 cm and a length of 30 cm was packed with 100 ml of a palladium-on-active alumina catalyst using spheres of γ-alumina 3 mm in diameter. The catalyst contained 0.5 wt % of Pd in Examples 1–3 and 5.0 wt % of Pd in Example 4. Then the reaction tube was placed in an electric furnace.

Preparatorily hydrogen gas was passed through the reaction tube packed with the catalyst at a rate of 100 ml/min for about 1 hr while the temperature of the reaction tube was maintained at 300–350° C. Then the temperature was lowered to 200° C., and the catalyst was pretreated with a mixed gas of R-114a and R-114 for 20 hr.

After the pretreatment of the catalyst the temperature of the reaction tube was adjusted to a predetermined reaction temperature shown in Table 1, and hydrogen gas was introduced into the tube at a rate of 198 ml/min while a mixed gas of 75 wt % of R-114a and 25 wt % of R-114 was introduced at a rate of 66 ml/min. That is, the molar ratio of hydrogen to dichlorotetrafluoroethane was 3:1. The product of the contact reaction was washed with water and then the organic substances in the washed gas were analyzed by gas chromatography. The results are shown in Table 1.

COMPARATIVE EXAMPLE 1

The reaction of Example 3 was modified only in that a palladium-on-active carbon catalyst was used. The catalyst used cylindrical pellets of active carbon 2 mm in diameter and 5 mm in length and contained 0.5 wt % of palladium. The result of the reaction was as shown in Table 1.

COMPARATIVE EXAMPLES 2 AND 3

The reaction of Example 1 was repeated except that the reaction temperature was raised and that the contact time was slightly varied. The particulars are shown in Table 1.

TABLE 1

| | Catalyst | Reaction Temp. (°C.) | Contact Time (sec) | Reaction Products (mol %) | | | | | | | Conversion of R114a/R-114 (%) | Selectivity to R-134a (%) |
| --- | --- | --- | --- | --- | --- | --- | --- | --- | --- | --- | --- | --- |
| | | | | R-114a | R-114 | R-134a | R-134 | R-124 | R-124a | R-143a | | |
| Ex. 1 | 0.5% Pd/γ-Al$_2$O$_3$ | 125 | 34 | 11.5 | 25.0 | 57.4 | — | 2.1 | — | 4.0 | 63.5 | 90.4 |
| Ex. 2 | " | 150 | 32 | 3.0 | 24.5 | 66.0 | — | 2.0 | — | 4.5 | 72.5 | 91.0 |
| Ex. 3 | " | 175 | 31 | 1.2 | 24.0 | 68.1 | — | 1.7 | — | 5.0 | 74.8 | 91.0 |
| Ex. 4 | 5% Pd/γ-Al$_2$O$_3$ | 175 | 31 | — | 22.4 | 69.8 | — | 1.9 | — | 5.9 | 77.6 | 90.0 |
| Comp. Ex. 1 | 0.5% Pd/C | 175 | 31 | 2.1 | 21.5 | 59.3 | 0.4 | 5.9 | 2.0 | 10.9 | 76.4 | 77.6 |
| Comp. Ex. 2 | 0.5% Pd/γ-Al$_2$O$_3$ | 200 | 28 | — | 19.1 | 69.0 | — | 2.9 | 0.5 | 8.5 | 81.9 | 84.2 |
| Comp. Ex. 3 | " | 250 | 26 | — | 12.3 | 57.6 | 3.5 | 6.6 | 7.7 | 12.3 | 87.7 | 65.7 |

We have succeeded in obtaining R-114a containing little R-114 from R-113a by using γ-alumina treated with hydrogen fluoride as catalyst. In conventional processes for vapor phase fluorination of halogenated hydrocarbons by reaction with hydrogen fluoride, it is prevailing to use chromium as the active metal of catalyst and alumina as the carrier. However, in the case of fluorinating R-113a the high activity of such a chromium catalyst on the reaction to substitute fluorine atom for chlorine atom becomes a demerit because R-114 and further fluorinated R-115 are by-produced with resultant lowering of the selectivity to aimed R-114a. It is known that aluminum fluoride has an activity on fluorinating reactions, but aluminum fluoride is unsuitable as a catalyst for forming R-114a from R-113a because of causing isomerization and disproportionation. Nevertheless we have discovered that partial fluorination of γ-alumina by treatment with hydrogen fluoride gives a catalyst very favorable for the conversion of R-113a into R-114a.

It is suitable to use spherical grains of γ-alumina about 5 mm in diameter. Such γ-alumina grains are first dried at about 250° C. or about to completely remove moisture and then subjected to treatment with hydrogen fluoride. It is suitable to use a mixed gas of hydrogen fluoride and nitrogen, and the treatment is made initially at about 200–300° C. and then at about 400° C. By such treatment about 60–80% of the γ-alumina will be fluorinated, and the resultant aluminum fluoride will be well distributed over the entire γ-alumina. Probably such results of the fluorinating treatment are the origin of the favorable catalytic activity of the treated γ-alumina.

For fluorination of R-113a, the catalyst prepared by the above treatment of γ-alumina is packed in a reaction tube which is usually made of nickel or stainless steel and maintained at a suitably elevated temperature, and a preheated mixed gas of R-113a and hydrogen fluoride is introduced into the reaction tube. At the reaction it is suitable to maintain the temperature of the reaction tube at 300–380° C. At temperatures below 300° C. the conversion of R-113a remains low, but at temperatures above 380° C. the formation of R-115 increases. It is suitable that the contact time is in the range from 2 to 100 sec for attaining sufficiently high conversion and without entailing unnecessary cost. The pressure in the reaction tube does not need to be specified and usually ranges from normal pressure to about 10 kg/cm². It is suitable to use 0.8 to 1.8 mol of hydrogen fluoride per mol of R-113a. If the amount of hydrogen fluoride is smaller the conversion of R-113a is insufficient. Use of more than 1.8 mol of hydrogen fluoride causes an increase in the amount of by-produced R-115 and resultant lowering of selectivity to R-114a.

By the above reaction R-114a is obtained at good yield. Since unreacted R-113a contained in the reaction product can easily be separated and recycled the ultimate yield of R-114a further increases. The catalyst has sufficient durability under the reaction conditions suitable for industrial practice. When the activity of the catalyst lowers by long use, it is possible to regenerate and reuse the catalyst by removing the adhering organic matter by a suitable treatment such as heating and then making a complementary treatment with hydrogen fluoride.

EXAMPLE 5

Initially 200 ml of γ-alumina spheres 5 mm in diameter was packed in a reaction tube of stainless steel having a diameter of 5 cm and a length of 50 cm. The reaction tube was heated up to 300° C. and kept at this temperature for 1 hr while nitrogen gas was continuously passed through the tube. After that a mixed gas of nitrogen and hydrogen fluoride was introduced into the reaction tube while the temperature was maintained at 300° C. When a hot-spot accompanying the fluorination of the γ-alumina in the reaction tube reached the outlet side the temperature of the reaction tube was raised to 400° C., and this temperature was maintained for 1 hr to thereby complete the preparation of a γ-alumina catalyst.

The temperature of the catalyst in the reaction tube was adjusted to and maintained at 300° C., and R-113a and hydrogen fluoride were introduced into the reaction tube each at a rate of 0.5 mol/hr. The reaction gas at the outlet of the reaction tube was analyzed by gas chromatography. The result is shown in Table 2. The reaction of R-113a with hydrogen fluoride was continued for 100 hr, but the catalyst in the reaction tube did not exhibit lowering of its activity.

EXAMPLES 6–9

The process of Example 5 was repeated except changes in the reaction temperature and/or the feed rate of hydrogen fluoride (i.e. molar ratio of HF to R-113a) as shown in Table 2. The results of the reaction are shown in Table 2.

TABLE 2

| | HF (mol/hr) | Temp. (°C.) | Reaction Products. (wt %) | | | | Conversion of R-113a (%) | Selectivity to R-114a (%) |
|---|---|---|---|---|---|---|---|---|
| | | | R-113a | R-114a | R-114 | R-115 | | |
| Ex. 5 | 0.5 | 300 | 44.4 | 55.5 | 0.1 | 0.1 | 55.6 | 99.8 |
| Ex. 6 | 0.5 | 330 | 37.9 | 61.9 | 0.1 | 0.3 | 62.2 | 99.7 |
| Ex. 7 | 0.5 | 360 | 31.6 | 67.0 | 0.1 | 1.4 | 68.4 | 98.0 |
| Ex. 8 | 0.9 | 360 | 18.1 | 80.2 | 0.4 | 1.3 | 81.9 | 97.9 |
| Ex. 9 | 0.7 | 360 | 26.7 | 71.9 | 0.3 | 1.1 | 73.3 | 98.1 |

In every example, the feed rate of R-113a was 0.5 mol/hr.

Also it is possible to use the γ-alumina catalyst prepared by treatment with hydrogen fluoride for the fluorination of R-113 to R-114a, though in this case a considerable amount of R-114 is formed together with R-114a.

EXAMPLE 10

The entire process of Example 7 was repeated except that R-113 (0.5 mol/hr) was used in place of R-113a.

The reaction gas at the outlet of the reaction tube contained 58.0 wt % of R-114a. The conversion of R-113 was 66.4%, and the yield of R-114a was 87.3% R-114a obtained by distillation of the reaction product contained 11.3 wt % of R-114.

The obtained R-114a (containing R-114) was subjected to hydrogenation reaction by the same method and under the same conditions as in Example 1.

After washing with water the reaction gas contained 13.6 mol % of R-114a, 11.3 mol % of R-114, 67.9 mol % of R-134a, 2.5 mol % of R-124 and 4.7 mol % of R-143a.

When it is desired to use R-113 as the starting material for preparing R-114a it is advantageous to first isomerize R-113 to R-113a, as mentioned hereinbefore, because by doing so the formation of R-114 can be suppressed.

The isomerization of R-113 to R-113a can be accomplished by either a liquid phase reaction comprising heating R-113 in the presence of a suitable catalyst such as aluminum chloride or a vapor phase reaction comprising contacting R-113 with aluminum fluoride heated to 250° C. or above. It is desirable to purify the R-113a obtained by an isomerization reaction, but it is permissible to directly subject the obtained R-113 containing R-113a to reaction with hydrogen fluoride to form R-114a. In the case of fluorinating a mixture of R-113a and R-113, it is probable that R-113a and most of R-113 turn into R-114a while the remaining portion of R-113 turns into R-114. In the fluorination reaction it is preferable to use partially fluorinated γ-alumina as catalyst.

EXAMPLE 11

A four-necked glass flask, which had a capacity of 1 liter and was provided with a stirrer and a reflux condenser, was charged with 500 g of R-113 and 20 g of anhydrous aluminum chloride employed as catalyst. The flask was heated while operating the stirrer to keep the liquid in the flask in a boiling state for 3 hr to thereby accomplish the isomerization of R-113 to R-113a.

The reaction liquid was washed with water and dried with calcium chloride, and then analysis was made by gas chromatography and $^{19}$F-NMR. The product contained 94.2 wt % of R-113a and 2.5 wt % of R-114a. The conversion of R-113 was 100%, and the yield of R-113a was 94.2%. By distillation of this crude product, R-113a of more than 99.9% purity was obtained.

Using the purified R-113a as the material for preparing R-114a, the entire process of Example 5 was repeated. The result was similar to the result of Example 5. That is, the conversion of R-113a was 55.6%, and the yield of R-114a was 99.8%. By taking into consideration the initial isomerization reaction of R-113, the yield of R-114a on the basis of R-113 was calculated to be 96.5%.

EXAMPLE 12

A reaction tube of glass 5 cm in diameter and 30 cm in length was held vertical, and a stirrer and a reflux condenser was provided to the reaction tube at the top. The reaction tube was charged with 400 ml of R-113 and 15 g of anhydrous aluminum chloride powder. Operating the stirrer the reaction tube was heated to keep the liquid in the tube boiling for 2 hr without distilling out. After that R-113 was dropped into the reaction tube at a rate of 5 g/min, while the reaction product was discharged from the reflux condenser so as to keep the liquid level in the reaction tube unchanged. After the lapse of 2 hr, continuing this operation, the reaction product was collected for 5 hr. The total quantity of the collected product reached 1,500 g. By analysis by gas chromatography and $^{19}$F-NMR the product contained 1.2 wt % of R-114a, 90.2 wt % of R-113a and 8.6 wt % of R-113.

Without purifying, the above reaction product was subjected to fluorination reaction by the same method and under the same conditions as in Example 6. The reaction gas at the outlet of the reaction tube contained 58.0 wt % of R-114a. The conversion of R-113a containing R-113 was 60.5 wt %, and the yield of R-114a on the basis of R-113 was 97.0%. By distillation of this crude product, R-114a containing 0.5 wt % of R-114 was obtained.

The obtained R-114a (containing R-114) was subjected to hydrogenation reaction by the same method and under the same conditions as in Example 3.

After washing with water the reaction gas contained 1.6 mol % of R-114a, 0.5 mol % of R-114, 89.2 mol % of R-134a, 2.2 mol % of R-124 and 6.5 mol % of R-143a.

In preparing R-114a by the fluorination of R-113a the reaction gas flowing out of the reactor contains unreacted hydrogen fluoride together with hydrogen chloride, R-114a and organic by-products. For the economical reason it is desirable to recover and reuse the unreacted hydrogen fluoride. It is a usual way to introduce the reaction gas into a separator provided with a cooler for separation of unreacted hydrogen fluoride from hydrogen chloride and organic matter. In that case it is necessary to cool the separator to a temperature lower than the boiling point of hydrogen fluoride. However, when the reaction gas contains R-113a, freezing of R-113a occurs in the separator, cooler or piping to result in choking of the gas passage. This is very dangerous.

We have solved the above problem about recovery of the unreacted hydrogen fluoride by adding R-113 to the reaction gas containing R-113a. The addition of R-113, which may be either vapor or liquid, is made at the outlet of the reactor in which R-113a is reacted with hydrogen fluoride in the presence of a catalyst. The temperature of R-113 to be added is variable according to the pressure in the reactor and preferably ranges from 100 to 200° C. when the reaction pressure ranges from normal pressure to about 10 kg/cm$^2$.

After the addition of R-113 the reaction gas is introduced into a separator provided with a cooler for separation into a gas phase containing R-114a formed by the fluorination reaction together with hydrogen chloride and by-products such as R-114 and R-115 and a liquid phase containing hydrogen fluoride, R-113 and R-113a. The gas phase is passed to a purifying apparatus for separating impurities from R-114a. The liquid phase separates into a hydrogen fluoride phase and an organic phase, so that hydrogen fluoride can easily be recovered. For separating the reaction gas into the gas phase and the liquid phase usually it is necessary to cool the separator to below 0° C. The freezing point of R-113a is 14° C. The addition of R-113 which has a freezing point of −35° C. is for preventing the freezing of R-113a by forming a mixture which is sufficiently low in freezing temperature. The object is accomplished by adding such an amount of R-113 that the molar ratio R-113/R-113a becomes 0.4 or above, though an optimum amount of addition is variable depending on the proportions of the other organic components of the reaction gas.

EXPERIMENT

Using the partially fluorinated γ-alumina catalyst prepared by the same method as in Example 5, R-113a was reacted with hydrogen fluoride by the same method and under the same conditions as in Example 5. At the outlet of the reaction tube the reaction gas contained 41.2 wt % of R-113a, 3.3 wt % of R-113, 55.5 wt % of R-114a, less than 0.1 wt % of R-114 and 0.1 wt % of R-115.

Without washing with water, the reaction gas was introduced into a cold-trap of chlorotrifluoroethylene maintained at −10° C. As a result the organic matter is the cold-trap froze, and hence the test had to be terminated immediately.

The above test was modified by adding R-113 to the reaction gas at the outlet of the reaction tube. When R-113 was added at a rate of 0.1 mol/hr whereby the molar ratio R-113/R-113a in the mixed gas became 0.57, cooling of the mixed gas to −10° C. in the cold-trap resulted in freezing of the organic matter in the trap. Next, the rate of addition of R-113 was increased to 0.2 mol/hr to increase the molar ratio R-113/R-113a to 1.05, but the result was similar. In the third run R-113 was added at a rate of 0.3 mol/hr to increase the molar ratio R-113/R-113a to 1.5. In the fourth run R-113 was added at a rate of 0.4 mol/hr so that the molar ratio R-113/R-113a became 2.0. In these two runs the cooling of the mixed gas to −10° C. did not cause freezing, and a liquid phase containing hydrogen fluoride was obtained. The liquid phase separated clearly into a hydrogen fluoride phase and an organic phase, so that hydrogen fluoride could easily be recovered.

What is claimed is:

1. A method of preparing 1,1,1,2-tetrafluoroethane, comprising reacting 1,1-dichloro-1,2,2,2-tetrafluoroethane with hydrogen gas in the presence of a palladium-on-active alumina catalyst at a temperature lower than 200° C. and not lower than 120° C.

2. A method according to claim 1, wherein said 1,1-dichloro-1,2,2,2-tetrafluoroethane contains not more than 25 wt % of 1,2-dichloro-1,1,2,2-tetrafluoroethane.

3. A method according to claim 2, wherein the proportion of hydrogen to said 1,1-dichloro-1,2,2,2-tetrafluoroethane is in the range from 2 to 4 by mol.

4. A method according to claim 1, wherein said catalyst contains 0.2 to 5 wt % of palladium.

5. A method according to claim 4, further comprising the step of treating said catalyst with dichlorotetrafluoroethane at an elevated temperature before the reaction of 1,1-dichloro-1,2,2,2-tetrafluoroethane with hydrogen.

6. A method according to claim 1, further comprising preparing said 1,1-dichloro-1,2,2,2-tetrafluoroethane by reacting 1,1,1-trichloro-2,2,2-trifluoroethane with hydrogen fluoride in vapor phase in the presence of a catalyst comprising γ-alumina partially fluorinated by treatment with hydrogen fluoride gas.

7. A method according to claim 6, wherein said treatment is made by contacting a mixture of hydrogen fluoride gas and nitrogen gas with γ-alumina at temperatures ranging from 200 to 400° C.

8. A method according to claim 6, wherein the reaction of 1,1,1-trichloro-2,2,2-trifluoroethane with hydrogen fluoride is carried out at a temperature in the range from 300 to 380° C.

9. A method according to claim 6, further comprising the steps of adding 1,1,2-trichloro-1,2,2-trifluoroethane for a reaction gas discharged from a reactor in which 1,1,1-trichloro-2,2,2-trifluoroethane is reacted with hydrogen fluoride and cooling the mixture of said reaction gas and 1,1,2-trichloro-1,2,2-trifluoroethane to a temperature lower than the boiling point of hydrogen fluoride.

10. A method according to claim 1, further comprising preparing said 1,1-dichloro-1,2,2,2-tetrafluoroethane by the steps of subjecting 1,1,2-trichloro-1,2,2-trifluoroethane to an isomerization reaction to form 1,1,1-trichloro-2,2,2-trifluoroethane and subjecting the product of said isomerization reaction to reaction with hydrogen fluoride in the presence of a fluorination catalyst.

11. A method according to claim 10, wherein said fluorination catalyst comprises γ-alumina partially fluorinated by treatment with hydrogen fluoride gas.

12. A method according to claim 11, wherein the reaction in the presence of said fluorination catalyst is carried out at a temperature in the range from 300 to 380° C.

13. A method according to claim 10, wherein said isomerization reaction comprises heating 1,1,2-trichloro-1,2,2-trifluoroethane in liquid phase in the presence of a catalyst.

14. A method according to claim 10, wherein said isomerization reaction comprises contacting vapor of 1,1,2-trichloro-1,2,2-trifluoroethane with heated aluminum fluoride.

* * * * *